(12) United States Patent
Kühn

(10) Patent No.: US 7,704,356 B2
(45) Date of Patent: Apr. 27, 2010

(54) GAS SENSOR ARRAY WITH ELECTROCHEMICAL GAS GENERATOR

(75) Inventor: Uwe Kühn, Wesenberg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 1038 days.

(21) Appl. No.: 11/379,880

(22) Filed: Apr. 24, 2006

(65) Prior Publication Data
US 2006/0283707 A1     Dec. 21, 2006

(30) Foreign Application Priority Data
Jun. 17, 2005    (DE) ................ 10 2005 028 246

(51) Int. Cl.
*G01N 27/404*    (2006.01)
*G01N 27/26*     (2006.01)
(52) U.S. Cl. .................. 204/401; 204/412; 204/415; 204/424; 73/1.06
(58) Field of Classification Search ............. 204/426, 204/401; 73/1.06
See application file for complete search history.

(56) References Cited
U.S. PATENT DOCUMENTS
4,444,645 A    4/1984   Deprez et al.

| 6,200,443 | B1* | 3/2001 | Shen et al. | 204/401 |
| 6,635,160 | B1* | 10/2003 | Dodgson | 204/401 |
| 2003/0145644 | A1* | 8/2003 | Rabbett et al. | 73/1.06 |

FOREIGN PATENT DOCUMENTS

| EP | 0 744 620 | 11/1996 |
| EP | WO 98/25139 | 6/1998 |
| GB | 2254696 A | 10/1992 |
| GB | WO 99/24826 | 5/1999 |
| GB | 2 362 959 | 12/2001 |
| GB | 2 407 870 | 5/2005 |

* cited by examiner

*Primary Examiner*—Harry D Wilkins, III
*Assistant Examiner*—Bryan D. Ripa
(74) *Attorney, Agent, or Firm*—McGlew and Tuttle, P.C.

(57) ABSTRACT

A compact gas sensor array, to which a test gas can be admitted without the use of mechanical components and whose readiness for measurement is interrupted during the calibration only briefly. The array includes a combination of an electrochemical gas sensor (3) and an electrochemical gas generator (2). A gas channel (1) is provided from the gas generator (2) to the measuring electrode (9) of the gas sensor (3). The measuring gas from the environment of the gas sensor (3) has free access to the measuring electrode (9).

19 Claims, 1 Drawing Sheet

GAS SENSOR ARRAY WITH ELECTROCHEMICAL GAS GENERATOR

CROSS REFERENCE TO RELATED APPLICATIONS

This application claims the benefit of priority under 35 U.S.C. §119 of German Patent Application DE 10 2005 028 246.6 filed Jun. 17, 2005, the entire contents of which are incorporated herein by reference.

FIELD OF THE INVENTION

The present invention pertains to a gas sensor array with a combination of a electrochemical gas sensor and a electrochemical gas generator.

BACKGROUND OF THE INVENTION

The particular test gas or measuring gas must be admitted to electrochemical gas sensors at regular intervals for checking the function or for calibration. This happens in practice, in general, manually from pressurized gas containers or with calibrating gas containers under normal pressure or also automatically by means of chemical or electrochemical gas generators, as is described, for example, in GB 2 254 696 A. The common feature of these processes is that the electrochemical gas sensor is not ready for measurement during the calibration.

SUMMARY OF THE INVENTION

The object of the present invention is to provide a compact gas sensor array with an electrochemical gas sensor, to which a test gas can be admitted for calibration or testing purposes without the use of mechanical components such as valves, wherein not only the electrochemical system, but also the path of the gas to the gas sensor can be checked and the readiness for measurement is not interrupted or is interrupted only briefly.

According to the invention, a gas sensor array is provided with a combination of an electrochemical gas sensor and an electrochemical gas generator. A gas channel from the gas generator to the measuring electrode of the gas sensor, wherein the measuring gas from the environment of the gas sensor has free access to the measuring electrode.

The measuring electrode may be covered with a porous or inherently permeable diffusion membrane. The electrodes of the gas sensor and of the gas generator may be connected to a control and evaluating unit.

The combination of a gas sensor, the gas generator and the gas channel may be connected in a mechanically detachable manner. The gas sensor and the gas generator may advantageously be arranged planarly next to one another. The gas sensor and the gas generator may advantageously have a circular cross section.

The gas channel may advantageously have a length of up to 30 mm and a cross-sectional area of 0.2 mm$^2$ to 5 mm$^2$. The diffusion membrane may advantageously consist of a polymer, especially PTFE.

The measuring electrode of the gas sensor and the working electrode of the gas generator are preferably arranged in one plane, and the test gas generated is sent to the electrochemical gas sensor via a gas channel. The gas channel protrudes into the area of the measuring electrode that is freely accessible due to diffusion of measuring gas from the environment of the gas sensor and is shaped such that the smallest possible area of the measuring electrode is hidden and test gas can be admitted frontally to the gas sensor. By connecting the gas generator via a control and evaluating unit, the complete gas sensor can be tested and it is subsequently immediately ready for measurement. The gas sensor can also remain in the measuring mode during the calibration by means of a plausibility check: Both the calibrating gas generation and the gas sensor signal are connected via the common control and evaluating unit. The quantity of test gas generated is proportional to the current flowing through the gas generator, so that the gas sensor also shows a proportional sensor current. If measuring gas is now supplied from the environment, the sensor current will be higher by a corresponding amount, so that the actual concentration of the measuring gas in the environment can be inferred in the knowledge of the generator current.

An exemplary embodiment of the present invention will be explained below on the basis of the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
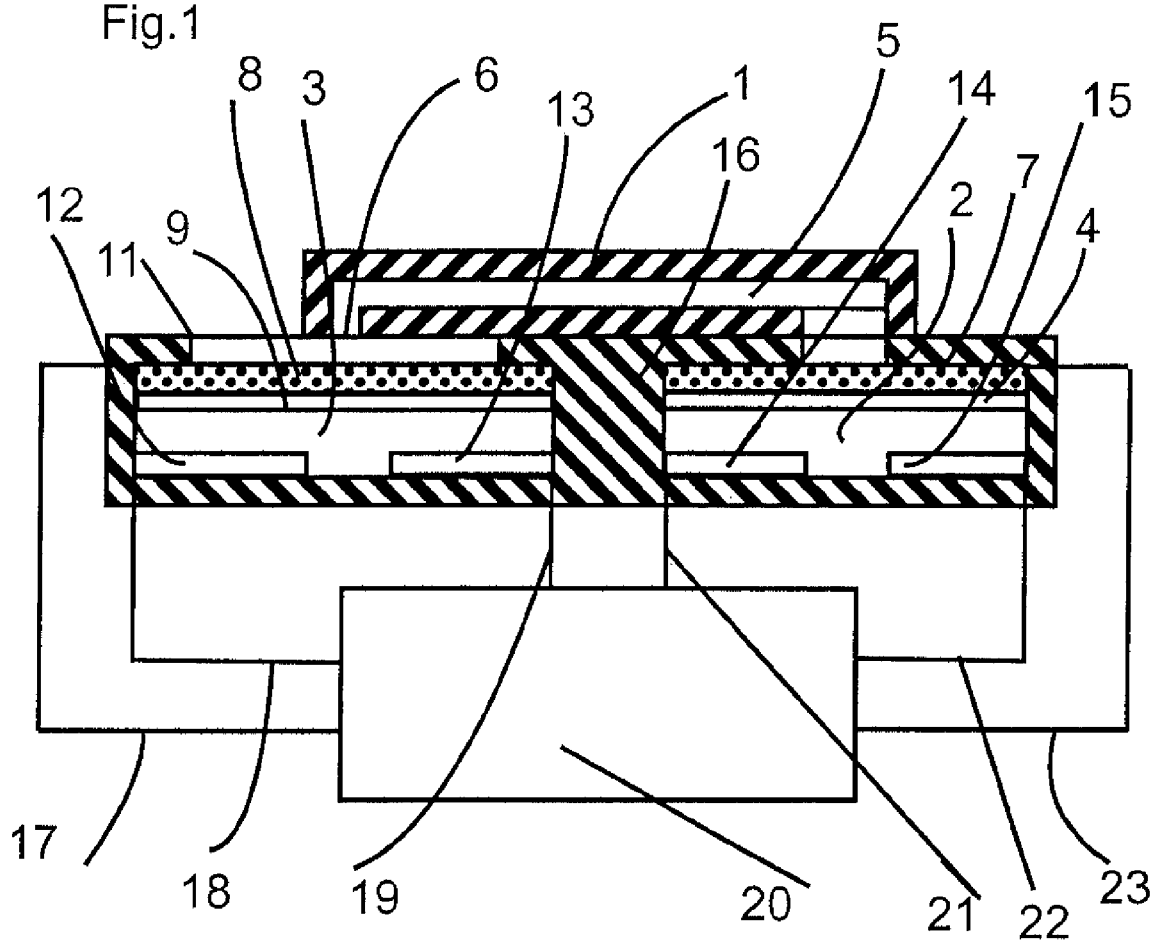
FIG. 1 is a sectional view through a gas sensor array according to the invention.
Figure 2:
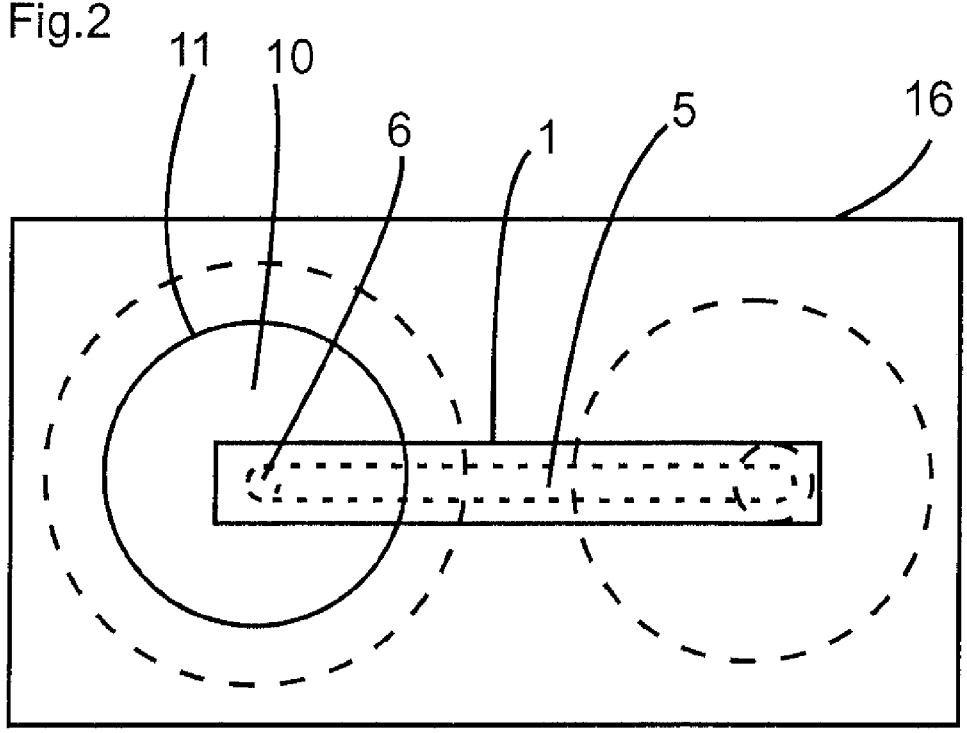
FIG. 2 is a top view of the array according to FIG. 1.

Referring to the drawings in particular, a gas generator 2 and an electrochemical gas sensor 3 are connected to one another on a gas side via a gas channel 1 such that test or calibrating gas generated in the gas generator 2 can reach the area of the measuring electrode 9 of the gas sensor 3. The measuring electrode 9 of the gas sensor 3 has an area that is freely accessible due to diffusion, without loss of gas. The test or calibrating gas is generated at the working electrode 4 of the gas generator 2. This gas diffuses through the porous or inherently permeable membrane 7 as well as the interior space 5 of the gas channel 1 to the porous or inherently permeable diffusion membrane 8. This gas is detected at the measuring electrode 9 of the gas sensor 3.

The opening 6 of the gas channel 1 protrudes into the area 10 of the measuring electrode 9 of the gas sensor 3. The area 10 is freely accessible due to diffusion of measuring gas from the environment of the gas sensor 3, and is preferably opened in the direction of that area and is arranged centrally. The gas channel 1 is shaped such that it hides as little of the accessible area 10 as possible.

The opening 6 of the gas channel 1 is preferably arranged, as a maximum, at the level of the housing edge 11 in order to minimize losses of gas into the environment and flow effects. The housing edge 11 can be artificially elevated, but this leads to a restriction of the spherical diffusion and thus to a reduction of the measured signal. Too tight an array with a distance of less than 0.5 mm of the opening 7 affects the free diffusion of the measuring gas to the gas sensor 3 and to the measuring electrode 9 and should therefore be avoided.

The gas generator 2 and the gas sensor 3 are accommodated in a compact manner in a housing 16 made of a plastic, for example, polypropylene, polyethylene or polytetrafluoroethylene, in order to keep the gas channel 1 as short as possible. For completeness' sake, the reference electrodes 12, 14 and the counterelectrodes 13, 15 of the electrochemical systems are shown as well. The generation of the calibrating gas and the gas sensor signal are switched via a common control and evaluating unit 20, which is connected to the electrodes of the two electrochemical systems by means of the connection lines 17, 18, 19 and 21, 22, 23.

The combination of the gas sensor 3, the gas generator 2 and the gas channel 1 may also have a modular design and may be connected in a mechanically detachable manner. In particular, the gas channel 1 may be designed as an independent connection part, which is attached if it is not an integral part of the housing 16. Preferred materials for the gas channel 1 are chemically resistant plastics with a smooth surface in order to avoid adsorption in the interior space 5.

The length of the gas channel 1 should not exceed 30 mm and the cross-sectional area through which free flow is possible should be between 0.2 $mm^2$ and 5 $mm^2$.

The electrodes of the gas sensor 3 are preferably platinum/PTFE composite electrodes.

The gas is generated in the gas generator 2 by applying an electric voltage between the working electrode 4 and the counterelectrode 15 of the gas generator 2. For example, hydrogen and oxygen are formed by the electrolysis of water. The hydrogen diffuses via the gas channel 1 to the gas sensor 3 and is detected there. As an alternative, a gas sensor 3 for measuring ammonia comprises, for example, three iridium electrodes with a suitable electrolyte, for example, a calcium nitrate solution.

The gas is generated in the gas generator 2 in this case by applying an electric voltage to the working electrode 4 and the counterelectrode 15, measured against the reference electrode 14 in an ammonium salt solution. The shift of the pH value leads to the release of ammonia, and this diffuses via the gas channel 1 to the gas sensor 3.

While specific embodiments of the invention have been shown and described in detail to illustrate the application of the principles of the invention, it will be understood that the invention may be embodied otherwise without departing from such principles.

What is claimed is:

1. A gas sensor array, comprising:
   a combination of an electrochemical gas sensor and an electrochemical gas generator, the combination including a housing with said electrochemical gas sensor surrounded by said housing except at a gas sensor opening area above a measuring electrode of the gas sensor, said sensor opening area being defined by a housing edge, said gas sensor opening area being fully in direct contact with an environment of the array; and
   a gas channel structure including a gas channel having a length of up to 30 mm extending from a gas generator opening to a channel discharge opening at said gas sensor opening area above said measuring electrode of the gas sensor, wherein said gas channel structure has a cross-sectional area of 0.2 $mm^2$ to 5 $mm^2$ and extends over a portion of said gas sensor opening area and the measuring gas from the environment of the gas sensor has free access to the measuring electrode through said gas sensor opening area that said gas channel structure does not extend over with said gas sensor opening area that said gas channel structure does not extend over directly in contact with the environment of the gas sensor array.

2. A gas sensor in accordance with claim 1, wherein the measuring electrode is covered with a porous or inherently permeable diffusion membrane.

3. A gas sensor in accordance with claim 1, wherein the electrodes of the gas sensor and of the gas generator are connected to a control and an evaluating unit.

4. A gas sensor in accordance with claim 1, wherein the combination of said gas sensor and said gas generator and said gas channel structure are connected in a mechanically detachable manner.

5. A gas sensor in accordance with claim 1, wherein said gas sensor and said gas generator are arranged planarly next to one another.

6. A gas sensor in accordance with claim 1, wherein said gas sensor and said gas generator have a circular cross section.

7. A gas sensor in accordance with claim 2, wherein said diffusion membrane consists of a polymer.

8. A gas sensor in accordance with claim 7, wherein said diffusion membrane consists of PTFE.

9. A gas sensor array, comprising:
   a housing defining a gas sensor cavity having a gas sensor opening area and defining an electrochemical gas generator cavity having a gas channel opening;
   an electrochemical gas sensor in said gas sensor cavity;
   an electrochemical gas generator in said electrochemical gas generator cavity;
   a gas channel structure with a gas channel, said gas channel structure extending from said gas channel opening to an outlet at or adjacent to said gas sensor opening area with said gas channel structure passing over only a portion of said gas sensor opening area such that at least a remainder of said gas sensor opening area of said gas sensor opening area that said gas channel structure does not pass over is in direct contact with an environment of the gas sensor array, wherein the measuring gas from the environment of the gas sensor has free access to a measuring electrode; and
   a gas permeable barrier or porous or inherently permeable diffusion membrane between said electrochemical gas sensor and said gas sensor opening area, said gas permeable barrier or porous or inherently permeable diffusion membrane being directly exposed to the environment of the gas sensor with no structure of the gas sensor array covering said gas permeable barrier or porous or inherently permeable diffusion membrane in a direction normal to a surface of said gas permeable barrier or porous or inherently permeable diffusion membrane except said gas channel structure such that structure of said gas sensor array does not interfere with free access to the measuring electrode of measuring gas from the environment of the gas sensor.

10. A gas sensor in accordance with claim 9, further comprising: a control and an evaluating unit wherein said electrochemical gas sensor includes said measuring electrode connected to said control and evaluating unit and said electrochemical gas generator includes an electrode connected to said control and evaluating unit.

11. A gas sensor in accordance with claim 9, wherein said housing and said gas channel are connected in a mechanically detachable manner.

12. A gas sensor in accordance with claim 9, wherein said gas sensor and said gas generator are arranged planarly next to one another.

13. A gas sensor in accordance with claim 9, wherein said gas sensor and said gas generator have a circular cross section.

14. A gas sensor in accordance with claim 9, wherein said gas channel has a length of up to 30 mm and a cross-sectional area of 0.2 mm² to 5 mm².

15. A gas sensor in accordance with claim 9, wherein said diffusion membrane consists of a polymer.

16. A gas sensor in accordance with claim 15, wherein said diffusion membrane consists of PTFE.

17. A gas sensor in accordance with claim 9, further comprising:
   a gas permeable barrier or porous or inherently permeable diffusion membrane between said electrochemical gas generator and said gas channel opening.

18. A gas sensor array, comprising:
   a housing defining a gas sensor cavity having a gas sensor opening area and defining an electrochemical gas generator cavity having a gas channel opening;
   an electrochemical gas sensor in said gas sensor cavity, said electrochemical gas sensor including a measuring electrode;
   an electrochemical gas generator in said electrochemical gas generator cavity, said electrochemical gas generator including a working electrode;
   a gas channel structure with a gas channel, said gas channel structure extending from said gas channel opening to said gas sensor opening area with said gas channel structure passing over only a portion of said gas sensor opening area such that at least a remainder of said gas sensor opening area, that said gas channel structure does not pass over, is in direct contact with gas in an environment of the gas sensor array, wherein the measuring gas from the environment of the gas sensor at least has free access to a measuring electrode through said gas sensor opening area that said gas channel structure does not pass over;
   a gas permeable barrier or porous or inherently permeable diffusion membrane between said electrochemical gas sensor and said gas sensor opening area, which gas permeable barrier or porous or inherently permeable diffusion membrane does not interfere with said free access to a measuring electrode of said measuring gas from the environment of the gas sensor wherein said permeable barrier or porous or inherently permeable diffusion membrane, that said gas channel structure does not pass over, is not covered by structure of the gas sensor array in a direction normal to said permeable barrier or porous or inherently permeable diffusion membrane and only said gas permeable barrier or porous or inherently permeable diffusion membrane is between said electrochemical gas sensor measuring electrode and said gas sensor opening area; and
   another gas permeable barrier or porous or inherently permeable diffusion membrane between said electrochemical gas generator and said gas channel opening.

19. A gas sensor array in accordance with claim 18, wherein said gas channel has a length of up to 30 mm and a cross-sectional area of 0.2 mm² to 5 mm².

* * * * *